United States Patent [19]  [11]  4,229,607
Gum et al.  [45]  Oct. 21, 1980

[54] PROCESS FOR RECOVERY OF ETHYLENE OLIGOMERS

[75] Inventors: Clarence R. Gum; Albert T. Kister, both of Houston, Tex.

[73] Assignee: Shell Oil Company, Houston, Tex.

[21] Appl. No.: 50,904

[22] Filed: Jun. 21, 1979

[51] Int. Cl.² .............................................. C07C 3/10
[52] U.S. Cl. .................................. 585/520; 585/523; 585/836
[58] Field of Search ........................ 585/520, 523, 836

[56] References Cited

U.S. PATENT DOCUMENTS

| | | | |
|---|---|---|---|
| 3,644,564 | 2/1972 | van Zwet et al. | 585/520 |
| 3,647,914 | 3/1972 | Glockner et al. | 585/520 |
| 3,647,915 | 3/1972 | Bauer et al. | 585/523 |
| 3,676,523 | 7/1972 | Mason | 585/523 |
| 3,686,351 | 8/1972 | Mason | 585/523 |
| 3,737,475 | 6/1973 | Mason | 585/523 |
| 3,825,615 | 7/1974 | Lutz | 585/523 |
| 4,020,121 | 4/1977 | Kister et al. | 585/504 |

*Primary Examiner*—C. Davis

[57] ABSTRACT

An improvement as described for the recovery of ethylene oligomers from the reaction product obtained when ethylene is oligomerized by contact in the liquid phase at elevated temperatures and pressures with a nickel complexed catalyst dissolved in an aliphatic diol solvent. In this improved process, the liquid oligomer product phase, after separation from gaseous and dissolved ethylene and liquid diol solvent, is subject to an aqueous acid wash followed optionally and preferably by a water wash to hydrolyze and extract diol solvent degradation products which carry through from the oligomerization reaction zone.

8 Claims, No Drawings

PROCESS FOR RECOVERY OF ETHYLENE OLIGOMERS

BACKGROUND OF THE INVENTION

This invention relates to an improved process for the production of linear alpha-olefins by oligomerization of ethylene. More particularly, this invention is directed to an improvement in the process for recovering ethylene oligomers from the reaction product obtained when ethylene is oligomerized by contact with a catalytic nickel complex dissolved in an aliphatic diol solvent.

Linear monoolefins are compounds of established utility in a variety of applications. Terminal linear monoolefins, particularly those having 12 to 20 carbon atoms per molecule, are known to be useful as intermediates in the production of various types of detergents e.g. alcohols, ethoxylates, etc.

Several synthetic techniques have been developed for the preparation of terminal linear monoolefins in the detergent range. One very attractive synthetic method from the standpoint of raw material availability and cost involves oligomerization of ethylene to higher molecular weight linear monoolefins (even numbered alpha-monoolefins) by contact with a catalytically active nickel complex dissolved in certain polar solvents. One class of suitable nickel complex catalysts for ethylene oligomerization is prepared as the reaction product of an olefinic nickel compound, including zero-valent nickel compounds such as bis(cyclooctadiene) nickel (O) or $\pi$-allyl nickel compounds, and a suitable bidentate ligand as described in U.S. Pat. No. 3,644,564 to Van Zwet et al, U.S. Pat. No. 3,647,914 to Glockner et al and U.S. Pat. No. 3,647,915 to Bauer et al. A different and preferred class of nickel complex catalysts can be prepared by contacting in certain polar organic solvents in the presence of ethylene (1) a simple divalent nickel salt which is at least somewhat soluble in the solvent, (2) a boron hydride reducing agent and (3) a suitable bidentate ligand. The preparation of catalysts in this preferred class and their use in ethylene oligomerization are described in U.S. Pat. Nos. 3,676,523, 3,686,351 and 3,737,457 to R. F. Mason and U.S. Pat. No. 3,825,615 to Lutz.

In cases where the oligomerization is carried out using the preferred nickel complex catalysts in a polar organic solvent, the reaction product typically consists of three phases: (1) a liquid solvent phase in which catalysts are dissolved; (2) a liquid hydrocarbon phase which consists of the total oligomer and includes dissolved ethylene, solvent and nickel complex catalyst and (3) gaseous ethylene. In early attempts to recover the oligomer product from this three-phase reaction product by a series of phase separations and flashing or distillation steps, it was discovered that the small amounts of residual catalyst present in the liquid hydrocarbon phase promoted the formation of objectionable, polymeric polyethylene when catalyst, solvent and ethylene are present in the hydrocarbon product phase at conditions under which part of the hydrocarbon phase is removed by flashing or distillation. As one means of preventing the formation of polyethylene, U.S. Pat. No. 4,020,121 to Kister et al discloses a stepwise process for recovery of ethylene oligomers from the oligomerization reaction product in which the liquid hydrocarbon product phase is subject to a scrubbing step using additional polar organic reaction solvent prior to the time that the catalyst-contaminated hydrocarbon phase is subjected to depressurization for removal of ethylene. In general terms, the overall recovery process described in the aforementioned U.S. Pat. No. 4,020,121 includes an initial degassing step wherein entrained ethylene gas is separated from the two liquid components of the oligomerization reaction mixture followed by phase separation of at least part of the solvent phase from the degassed liquid to afford a liquid hydrocarbon phase substantially free of solvent. According to the patent teaching, this separated liquid hydrocarbon product phase is subsequently passed to a product scrubber where it is contacted with a stream of pure oligomerization reaction solvent under sufficient pressure to avoid flashing of dissolved ethylene, said solvent serving to remove residual active catalyst from the hydrocarbon phase. After removal of the residual active catalyst, the separated hydrocarbon product is passed to a deethenizer for removal of dissolved ethylene and the deethenized product is water-scrubbed to remove residual, dissolved or entrained solvent thereby affording an oligomer product essentially free of solvent, catalyst and ethylene. In this process scheme, the separated ethylene gas and a substantial portion of the solvent phase containing active catalyst complex are suitably recycled to the oligomerization zone with the remainder of the separated solvent being passed to a solvent recovery zone in which purified solvent is produced.

While the processing scheme described in the aforementioned U.S. Pat. No. 4,020,121 provides an attractive means of recovering ethylene oligomers from oligomerization reactions employing nickel complex catalysts in polar organic solvents, it is not completely free of problems. In particular, when aliphatic diols are employed as the source of polar organic solvent in the oligomerization reaction, it has been found that small amounts of oxygenated degradation products are formed from the diol solvent during oligomerization and/or in subsequent processing which carry through the recovery scheme and appear as contaminants in the separated oligomer product. At least some of these contaminants which are typically oxidized and/or condensed are derivatives of the aliphatic diol solvent (carbonyl compounds, acetals and hemiacetals), have boiling points and solubilities sufficiently similar to the produced oligomers that they are very difficult to remove from the oligomer product. For example, when a preferred oligomerization solvent such as 1,4-butanediol is employed, a series of furan-type impurities are formed which have solubility and boiling points quite similar to the oligomer product in the detergent range ($C_{12}$–$C_{20}$). Unless these oxygenated impurities are somehow removed, they will appear as contaminants in the final oligomer product in cases where the oligomers are recovered directly or, they may act as catalyst poisons in cases where the oligomer product, or a portion thereof, is subject to further processing such as sequential isomerization and disproportionation described in U.S. Pat. No. 3,766,939 to Berger.

Accordingly, it would be highly desirable, if the oligomer product recovery scheme heretofore employed to separate oligomer from diol solvent, nickel complex catalyst, and excess ethylene could be modified so that the diol solvent degradation products are substantially eliminated as a source of oligomer product contamination. Further, it would be especially advantageous if this source of oligomer product contamination could be minimized or eliminated in a way which does not materially increase the cost and complexity of the process.

SUMMARY OF THE INVENTION

A relatively simple and economic means has now been found to eliminate the minor amounts of diol solvent degradation products which appear in the oligomer product phase recovered from a reaction zone wherein ethylene is oligomerized at elevated temperature and pressure by contact with a solution of a nickel complex catalyst in an aliphatic diols solvent. With this process improvement, which is advantageously employed as a modification to the oligomer recovery process described in the aforementioned U.S. Pat. No. 4,020,121, the diol degradation products are substantially removed from the oligomer product phase by contacting the contaminated oligomer product with an acidic water solution after it has been separated from substantially all of the residual diol solvent, nickel complex catalyst and unreacted ethylene. In particular, it has been found that an acidic water solution having a pH below about 5 will catalyze hydrolytic decomposition of the diol degradation products into lower molecular weight oxygenated products (alcohols and aldehydes) which are then readily extracted into the aqueous phase to afford an oligomer product phase substantially free of diol solvent degradation products. To insure the most complete removal of hydrolyzed diol degradation products, the oligomer product recovered from the initial aqueous acid wash is advantageously passed through at least one additional acid wash and then on to a water scrubbing zone where water is used to extract any trace portions of hydrolyzed diol degradation products and residual acid which carry through the staged acid wash. This staged hydrolysis and extraction procedure employing a water scrubbing step subsequent to the staged aqueous acid contacting procedure is an optional and preferred embodiment of the invention.

Accordingly, the instant invention provides an improved process for the oligomerization of ethylene to linear alpha-olefins wherein ethylene is oligomerized by contact in the liquid phase at elevated temperature and pressure with a solution of an oligomerization catalyst composition comprising catalytically active nickel complex in an aliphatic diol solvent to afford a reaction product made up of (1) a liquid solvent phase containing dissolved catalyst, (2) a liquid hydrocarbon phase comprising ethylene oligomers or linear alpha-olefins containing dissolved ethylene, catalyst and diol solvent degradation products; and (3) a gaseous ethylene phase, said ethylene oligomers being recovered by separating the liquid hydrocarbon phase from the gaseous ethylene phase and at least part of the liquid solvent phase under pressure, after which the separated liquid hydrocarbon phase is sequentially washed with sufficient aliphatic diol solvent to remove any residual active catalyst, subjected to reduced pressure to flash off dissolved ethylene and scrubbed with water to remove residual solvent; characterized by the improvement which comprises, contacting the liquid hydrocarbon phase immediately after water scrubbing with sufficient aqueous acid at elevated temperature to hydrolyze and extract the diol solvent decomposition products, said aqueous acid having a pH below about 5.

DESCRIPTION OF THE PREFERRED EMBODIMENTS

The improvement according to the invention is broadly applicable to any processing scheme wherein ethylene is oligomerized by contact with a catalytic nickel complex dissolved in an aliphatic diol solvent and the three phase reaction product is processed to recover an oligomer or linear alpha olefin product which is substantially free of catalyst, diol solvent and ethylene but contains a minor amount of diol solvent degradation products generated during the oligomerization and/or subsequent product and solvent recovery. In this regard, the improvement according to the invention is most suitably employed in conjunction with the oligomer recovery process disclosed in U.S. Pat. No. 4,020,121 to Kister et al. As noted previously, U.S. Pat. No. 4,020,121 teaches a stepwise oligomer recovery process which substantially eliminates the formation of unwanted, by-product polyethylene during product recovery phase through the removal of trace amounts of active catalyst from the liquid hydrocarbon product phase by means of a polar (diol) reaction solvent wash prior to the time that the catalyst-contaminated hydrocarbon phase is subjected to depressurization for removal of ethylene. The disclosure of U.S. Pat. No. 4,020,121 with respect to the sequence of processing steps and associated process conditions employed to oligomerize ethylene into a range of linear alpha olefins (oligomers) and to recover the oligomer product from the three phase of oligomerization reaction product is herewith incorporated by reference.

In basic terms, the process of U.S. Pat. No. 4,020,121 provides for the recovery of oligomer product from the three phase oligomerization reaction effluent made up of (1) a liquid diol solvent phase containing dissolved nickel complex catalyst, (2) a liquid hydrocarbon phase which consists of total oligomer and includes dissolved ethylene, solvent and nickel complex catalyst and (3) gaseous ethylene by (a) feeding the reaction effluent to a gas-liquid separation zone wherein gaseous ethylene is separated from the liquid product at temperatures and pressures approximating the reaction zone conditions; (b) passing the separated liquid product comprising the liquid solvent phase and hydrocarbon phase to one or more liquid-liquid separation zones in which a substantial portion of liquid diol solvent and catalyst complex are removed to afford a liquid hydrocarbon product phase containing dissolved ethylene and a small amount of solvent and catalyst complex; (c) scrubbing the phase separated liquid hydrocarbon product with purified or fresh diol reaction solvent under sufficient pressure to avoid flashing of dissolved ethylene, said solvent serving to remove residual active catalyst from the hydrocarbon phase; (d) passing the catalyst-free, hydrocarbon product to a deethenizer wherein dissolved ethylene is flashed off at reduced pressure to afford a deethenized hydrocarbon product containing minor amounts of diol solvent; and (e) washing the deethenized product with water to remove residual diol solvent thereby affording a liquid oligomer product essentially free of solvent, catalyst and ethylene. In this process configuration, the separated ethylene gas and a substantial portion of the solvent phase containing active catalyst are suitably recycled to the oligomerization reaction zone with the remainder of the separated solvent being passed to a solvent recovery zone in which purified solvent is produced. Further, the purified (water-scrubbed) oligomer is suitably passed to a product work-up system for recovery of the desired oligomer fractions, said product work-up system typically consisting of a series of fractionating columns. When the improvement according to the invention is integrated with the oligomer recovery process of U.S. Pat. No. 4,020,121, the aqueous acid scrubbing of the oligomer product described herein is suitably carried out on the water scrubbed product, although aqueous acid scrubbing of the oligomer (hydrocarbon) product at any point in the process of U.S. Pat. No. 4,020,121 after phase separation from the solvent phase is not precluded. In fact, under certain conditions, it may be preferable to replace the final water washing step in the process of U.S. Pat. No. 4,020,121 with the aqueous acid scrubbing step of the present invention.

The process of the invention can be used to advantage with any oligomerization reaction system which employs the nickel complex catalysts described in the "Background of the Invention" in an aliphatic diol solvent under conditions which lead to the formation of measurable quantities of diol solvent degradation products. Preferably, the ethylene oligomerization is carried out using a nickel complex catalyst prepared by reacting a bidentate chelating ligand with a simple divalent nickel salt and boron hydride reducing agent in the presence of ethylene in an aliphatic diol solvent. Preparation and use of catalysts of this type are described in U.S. Pat. Nos. 3,676,523, 3,686,351, and 3,737,475 all to R. F. Mason and 3,825,615 to Lutz. In accordance with these patent disclosures, it is preferred to form the nickel complex catalyst with bidentate chelating ligands having a tertiary organophosphorus moiety with a suitable functional group substituted on a carbon atom attached directly to or separated by no more than two carbon atoms from the phosphorus atom of the organophosphorus moiety. Representative ligands of this type are compounds of the general formula:

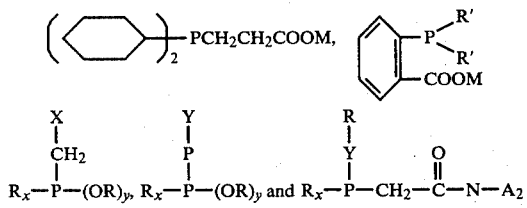

wherein
R, independently, is a monovalent organo group,
R' a monovalent hydrocarbyl group,
X is carboxymethyl or carboxyethyl;
Y is hydroxymethyl, mercaptomethyl, hydrocarbyl of up to 10 carbon atoms or hydrycarbyloxycarbonyl of up to 10 carbon atoms;
A is hydrogen or an aromatic group of up to 10 carbon atoms;
M is hydrogen or an alkali metal, preferably sodium or potassium;
x and y are zero, one or two and the sum of x and y is two, with the proviso that when x is two the R groups may together with the phosphorus atom form a mono- or bicyclic heterocyclic phosphine having from 5 to 7 carbon atoms in each ring thereof.

Particularly preferred complexes are those described in U.S. Pat. No. 3,676,523 in which the ligand is an o-dihydrocarbyl-phosphinobenzoic acid or its alkali metal salt and most preferably o-diphenylphosphinobenzoic acid; in another preferred complex, described in U.S. Pat. No. 3,825,615, the ligand is dicyclohexylphosphinopropionic acid or its alkali metal salt.

The molar ratio of nickel to bidentate ligand in the preparation of the nickel complex catalyst is preferably at least 1:1, i.e. the nickel is present in equimolar amount or in molar excess. In the preparation of catalyst complexes from a nickel salt, a ligand and boron hydride reducing agent, the molar ratio of nickel salt to ligand is suitably in the range from 1:1 to 5:1 with molar ratios of about 1.5:1 to 3:1 preferred and ratios of about 2:1 especially suitable. In these preparations, the boron hydride is suitably present in equimolar amount or molar excess relative to the nickel salt. There does not appear to be a definite upper limit on the boron hydride/nickel ratio, but for economic reasons it is preferred not to exceed a ratio of 15:1; the preferred ratio is usually between about 1:1 and about 10:1 with a ratio of about 2:1 specially preferred; ratios somewhat below 1:1 are also suitable.

The nickel complex catalysts are suitably preformed by contacting the catalyst precursors in the presence of ethylene in a suitable polar organic diluent or solvent which is not reduced by the boron hydride reducing agent. Preferably, the solvent used in the catalyst preparation is an aliphatic diol, most preferably the aliphatic diol employed as the reaction solvent in the oligomerization process. In a preferred modification of producing the preferred catalyst complexes as detailed in the patents to Mason and Lutz, supra, the solvent, nickel salt and ligand are contacted in the presence of ethylene before the addition of boron hydride reducing agent. It is essential that such catalyst compositions be prepared in the presence of ethylene. The catalysts are suitably prepared at temperatures of about 0° C. to 50° C., with substantially ambient temperatures e.g. 10° C.–30° C. preferred. The ethylene pressure and contacting conditions should be sufficient to substantially saturate the catalyst solution. For example, ethylene pressures may be in the range from 10 to 1,500 psig or higher. Substantially elevated ethylene pressures, e.g. in the range from 400 to 1,500 psig are preferred.

The solvent employed in the oligomerization reaction phase of the process according to the invention is an aliphatic diol of 2 to 7 carbon atoms. Suitable aliphatic diols include vicinal alkane diols such as ethylene glycol, propylene glycol, 2-methyl-1,2-propanediol, 1,2-butanediol and 2,3-butanediol and alpha-omega alkane diols such as 1,4-butanediol, 1,5-pentanediol, 1,6-hexanediol and 1,7-heptandiol. Alpha-omega alkane diols of 4 to 6 carbon atoms are preferred solvents with 1,4-butanediol being particularly preferred. In some cases it may be desirable to employ mixtures of the above-mentioned alkane diols as the solvent source for the reaction.

The oligomerization reaction can be carried out in a batch or continuous manner and is suitably conducted at temperatures in the range from about 25° C. to 150° C., but preferably from about 70° C. to 100° C. The pressure must be at least sufficient to maintain the reaction mixture substantially in liquid phase although excess ethylene will be present in vapor phase. Pressures in the range from about 300 psig to 5,000 psig may be employed. Other than for maintaining the liquid phase condition of the system, the total pressure is less significant than the partial pressure of ethylene, which is a primary factor in maintaining the desired ethylene concentration in the solvent phase where the oligomerization reaction takes place. In the preferred system, the ethylene partial pressure is suitably in the range from about 400 psig to 2,500 psig and preferably between about 1,000 and 2,500 psig. The concentration of catalyst, calculated as nickel metal, in the solvent phase is at least about 0.0005 molar and suitably from about 0.0005 to 0.001 molar.

When the oligomerization reaction is carried out at higher temperatures, that is temperatures at or above the preferred range, it has been found that the diol solvent employed has a tendency to undergo certain reactions e.g., dehydration and dehydrogenation, leading to the formation of degradation products. This tendency towards the formation of diol solvent degradation products is especially pronounced in the case of a continuous oligomerization reaction system such as that specified in U.S. Pat. No. 4,020,121 where reaction solvent is continuously recovered from the oligomerization reaction product and recycled along with dissolved active catalyst back into the reaction zone. In this continuous reaction system which is employed in a preferred aspect of the present invention, recycle of reaction solvent increases the residence time of the diol solvent at higher temperatures with a consequent build up of diol degradation products. Further opportunity exists for formation of additional quantities of diol solvent degradation products during the product recovery phase of the process of U.S. Pat. No. 4,020,121 since at least some of the product recovery steps are typically carried out at elevated temperature.

As noted above, the diol solvent degradation products are typically oxygenated materials formed by loss of hydrogen and/or water from the solvent molecule. With the preferred alpha, omega-alkanediol reaction solvents, the predominant degradation products are acetals and hemiacetals. For example, 1,4-butanediol, the most preferred diol reaction solvent, typically forms a variety of cyclic acetals and hemiacetals including 2-hydroxytetrahydrofuran, 2,2-oxybistetrahydrofuran, 2-(4-hydroxybutyloxy)tetrahydrofuran and 1,4-bis (2-tetrahydrofuryloxy)butane as the principle degradation products. In a continuous oligomerization reaction and product recovery system such as is disclosed in U.S. Pat. No. 4,020,121 where the reaction is carried out at steady state conditions at a temperature within the preferred range (70° to 100° C.) the total quantity of diol degradation products present in the recovered oligomer product can range as high as 0.2% by weight of the full range oligomer product. Depending on the boiling points of the various degradation products formed, a further concentration of the diol derived impurities in one or more oligomer fractions can occur when the full range oligomer product is split into single or narrow range carbon numbers for further processing and/or use. This is particularly true for the oligomer fraction in the detergent range which is recovered from a continuous oligomerization using 1,4-butanediol as the reaction solvent. Here, the butanediol derived impurities concentrate to a level in the detergent range alpha olefin fraction which is approximately 10 times that found in the full range oligomer product.

The acid hydrolysis and extraction procedure of the invention is most suitably carried out on the oligomer product containing minor amounts of diol degradation products after it has been separated from substantially all of the diol reaction solvent, nickel complex catalyst and gaseous and entrained ethylene. To effect hydrolysis of the diol degradation products and consequent extraction of the hydrolyzed degradation products from the oligomer product, the contaminated product is contacted in the improvement according to the invention with an acidic water solution having a pH below about 5, preferably between about 3.5 and about 4.5. The residence time for this hydrolysis and extraction step will depend on several factors including the temperature employed, the weight ratio of aqueous acid to hydrocarbon, the pH of the aqueous acid and the desired degree of impurity removal. Suitably, the contact time is sufficient to afford substantially complete hydrolysis of the contained diol degradation products. Under the reaction conditions contemplated by the invention, contact times of from about 10 to about 60 minutes are sufficient to effect hydrolysis and extraction. For most efficient hydrolysis and extraction, it is desirable to carry out the acid contacting step at elevated temperature with temperatures in the range of about 80° to about 120° C. being preferred. Most preferably, the aqueous acid contacting step is conducted at a temperature of from 95° to 110° C. The weight ratio of aqueous acid to hydrocarbon (oligomer) phase employed in this hydrolysis and extraction procedure may vary over wide limits depending on the residence time and process equipment sizing. Suitably, the weight ratio of aqueous acid to hydrocarbon treated ranges between 0.2:1 and 2:1 based on the weight of water in the aqueous acid. Preferably the weight ratio of water (in aqueous acid) to hydrocarbon is about 0.5:1.

The aqueous acid employed in the hydrolysis and extraction procedure of the invention is a dilute aqueous solution of an acid and/or acid salt having a pH within the desired range. Suitable acid sources include inorganic acids such as phosphoric, sulfuric and boric acid; organic acids such as carbonic, formic, oxalic, acetic and citric acid and acid salts such as potassium dihydrogen phosphate, potassium hydrogen phthalate, sodium dihydrogen phosphate, and sodium hydrogen phosphite. Preferably the source of acid used is phosphoric acid. Mixtures of acid salts and acids may be employed, for example, sodium dihydrogen phosphate and phosphoric acid.

The acid hydrolysis of diol degradation products and extraction of the hydrolyzed materials may be carried out in either batch or continuous fashion. In a typical batch operation, the oligomer product, substantially free of solvent, catalyst and ethylene and the aqueous acid are separately charged to a tank or vessel equipped with an agitator and suitable means for maintaining the desired temperature for hydrolysis, e.g., steam coils. After the desired weight ratio of aqueous acid to hydrocarbon is obtained, the acid and hydrocarbon are placed into intimate contact by agitation for a period of time sufficient to achieve substantially complete hydrolysis and extraction of hydrolyzed products into the aqueous phase. Upon completion of the residence time for hydrolysis and extraction, typically 10 to 60 minutes, the agitation is terminated and the hydrocarbon and aqueous acid containing the hydrolyzed diol degradation products are allowed to phase separate. After phase separation, the aqueous phase containing the hydrolysis products is withdrawn from the bottom of the contacting vessel and the remaining hydrocarbon (oligomer) phase, now substantially free of diol degradation products, can be passed to product finishing and/or further processing. In this batch operation, a single processing vessel serves as both a mixer and a settler such that hydrolysis, extraction and separation of the extracted products can be effected without the need for additional processing equipment. Preferably, the acid hydrolysis and extraction according to the invention is carried out in a continuous manner. One method for continuous operation suitably employs a series of mixer/settler vessels, such as are described for the batch process above, in parallel alignment so that while one vessel is being filled, the hydrolysis and extraction and the phase separation aspects of the process operation can be effected in one or more separate mixer/settlers. Preferably the continuous operation is carried out using a process configuration in which the aqueous acid contacting, i.e., hydrolysis and extraction, and the phase separation are performed as separate process steps. In this preferred process embodiment the contaminated hydrocarbon product and aqueous acid are continuously passed at the selected weight ratio to a mixing vessel of sufficient size to afford the desired residence time for hydrolysis and extraction. This mixing vessel may be of any conventional design, for example an externally heated pipeline reactor equipped with static mixing devices or an agitated tank equipped with steam coils or some suitable heating means. To complete this continuous process, a portion of the aqueous acid and hydrocarbon mixture is continuously withdrawn from the mixing vessel at a point remote from the inlet and passed to a phase separation vessel with outlets above and below the phase separation surface for removal of purified hydrocarbon (oligomer) and aqueous acid containing hydrolyzed diol degradation products respectively.

As noted previously, a preferred embodiment of the present invention relates to a staged hydrolysis and extraction procedure in which the hydrocarbon or oligomer product phase containing minor amounts of diol degradation products is passed to more than one, preferably two, aqueous acid contacting steps and the hydrocarbon product obtained thereby is further extracted with water in an optional water scrubbing zone. In this preferred embodiment, the second and/or subsequent acid contacting steps are suitably carried out using process equipment and conditions which are substantially identical to that used in the initial acid contacting step (see above). The subsequent water washing of the oligomer product from the stated aqueous acid hydrolysis and extraction procedure facilitates more complete extraction of any trace portions of hydrolyzed diol degradation products which carry through the staged acid wash as well as assuring removal of any entrained aqueous acid. This optional water washing of the recovered oligomer phase from acid hydrolysis and extraction may be carried out batchwise or continuously and suitably employs process facilities which are similar in design to those used in the aqueous acid contacting step. The temperature at which this water washing of the oligomer phase is conducted may vary over a wide range, for example, from 80° to 130° C. Preferably, the water washing is carried out at a temperature within the range described for the acid contacting step, that is from about 80° to about 120° C. The weight ratio of water to oligomer or hydrocarbon phase employed in the water scrubbing operation (or each water scrubbing stage in a multistage operation) suitably ranges between 0.2:1.0 and 2.0:1.0, water charged to hydrocarbon treated. The contacting or mixing time used to effect extraction of residual hydrolyzed diol degradation products and entrained acid from the hydrocarbon phase into the water phase typically ranges from 10 to 100 minutes. In this regard, it is convenient and thus preferred to use a contacting time which is subsequentially equivalent to that employed in each stage of the aqueous acid contacting procedure, that is from 10 to 60 minutes. Upon completion of the contact time (under agitation) selected for water extraction, the phases are allowed to phase separate and the washed hydrocarbon and water phases are separately recovered. When the optional water wash of the hydrocarbon product from the acid hydrolysis and extraction is incorporated into the preferred continuous process according to the invention with its separate mixing and phase separation zones, the water washing stage is preferably conducted in a manner similar to the acid wash with separate process zones for contacting or mixing of the water and hydrocarbon and for phase separation of the agitated mixture. Most preferably a single water washing stage is employed following two acid contacting stages in this preferred continuous process with the hydrocarbon phase being recovered from the phase separator of the second acid contacting stage and subsequently passed to the mixing zone of the water washing stage.

The aqueous acid hydrolysis and extraction procedure according to the invention is effective in removing the diol reaction solvent degradation products conventionally present in the recovered oligomer product down to levels of less than about 5 ppm based on the full range olefin product. These diol degradation products which typically include cyclic and condensed oxygenated derivatives of the diol solvent e.g., acetals and hemacetals, are not sufficiently soluble in aqueous media to be removed down to tolerable levels by water extraction alone. However, the aqueous acid acting as a hydrolysis catalyst effectively breaks down these cyclic and condensed derivatives into lower molecular weight aldehydes and alcohols, including the diol solvent, itself, which are more readily soluble and extractable into the aqueous phase.

The effectiveness of the aqueous acid hydrolysis and extraction process of the invention in removing diol reaction solvent degradation products from the recovered oligomer phase of the oligomerization product is demonstrated in the following illustrative embodiments.

ILLUSTRATIVE EMBODIMENT I

To demonstrate the improvement according to the invention, typical full range oligomer product recovered substantially free of reaction solvent, nickel complex catalyst and ethylene by the process of U.S. Pat. No. 4,020,121 was contacted with aqueous media at various pHs using the hydrolysis and extraction procedure of the invention. The source of oligomer product for these tests was a continuous ethylene oligomerization reaction in 1,4-butanediol reaction solvent using a nickel complex catalyst prepared by reacting diphenylphosphinobenzoic acid with nickel chloride hexahydrate and sodium borohydride in the presence of ethylene and 1,4-butanediol. The conditions for this ethylene oligomerization reaction included a reaction temperature of 95° C. and pressure of 1500 psig in a 3-stage pipeline reactor (total residence time on a once through basis of 12 minutes) with interstage cooling. Using the process of U.S. Pat. No. 4,020,121, ethylene gas and the catalyst-containing diol solvent phase were continuously separated from the 3-phase reaction mixture in a series of phase separation zones and recycled to the reaction zone. The remaining steps of the oligomer or hydrocarbon phase recovery were carried out substantially as described in the Example given in U.S. Pat. No. 4,020,121 i.e. diol solvent scrubbing under pressure followed by deethenization and water washing of the oligomer product.

The full range oligomer product ($C_4$–$C_{60+}$) subject to hydrolysis and extraction at various pH's (both within and above the acidic pH range of the invention) contained the following approximate quantities of diol solvent degradation products.

| Diol Degradation Product | Concentration Parts Per Million by Weight |
|---|---|
| 2-hydroxytetrahydrofuran | 100 |
| 2,2-oxy-bistetrahydrofuran | 7 |
| 2-(4-hydroxybutyloxy) tetrahydrofuran | 435 |
| 1,4-bis(2-tetrahydrofuryloxy)butane | unknown |

Since 2-(4-hydroxybutyloxy)tetrahydrofuran was the major diol degradation product observed, the effectiveness of the hydrolysis and extraction procedures tested in removing the diol degradation products was evaluated on the basis of the extent to which this impurity was removed.

The hydrolysis and extraction tests were carried out using a one-stage system comprising a mixing vessel and a phase separator. The mixing vessel employed was a 300 ml Magnedrive autoclave, 2" ID by 6" high, made of type 316 stainless steel. This vessel was equipped with a standard shrouded mixing impeller near the bottom and a marine propeller mounted about halfway up the central stirrer shaft. The stirrer was operated at 1500 rpm during the mixing stage of the process and the vessel was held liquid full during the entire test. The mixing vessel was further equipped with inlet and outlet ports, a sample line for mixed liquid and a thermocouple. The phase separator, connected to the outlet port of the mixer, was a 100 ml glass vessel equipped with an inlet for the mixed liquid and outlets for the separated hydrocarbon and aqueous phases. The hydrocarbon and aqueous feeds for each experiment were charged to four liter Hoke cylinders which act as blowcases. The feeds were pressured from the cylinders by nitrogen through calibrated orifices and small motor valves into the mixing vessel. During a typical test, the system was operated at 50 psig with the two streams being separately charged to the mixer at the desired weight ratio and the mixed stream being passed after the desired residence time to the phase separator where separated aqueous phase was taken off on level control and the hydrocarbon phase on pressure control.

The specific conditions employed in the extraction and hydrolysis tests are given in Table I below. In all cases the temperature during the mixing stage was maintained at about 93° C. while the residence time ranged between 25 and 43 minutes in the mixing vessel and the weight ratio of aqueous phase:hydrocarbon phase varied between 0.4:1 to 0.65:1. The pH of the aqueous extractants tested ranged between 4.9 and 7.9 as measured by the pH of the aqueous extract leaving the phase separator. The pHs on the acidic side were obtained by using dilute solutions (0.2% or 0.025% by weight) of sodium dihydrogen phosphate in distilled water. The quantity of diol degradation product in oligomer or hydrocarbon phase before and after treatment was determined by gas-liquid chromatography.

| Test Number | Aqueous Phase Used | pH of Aqueous Phase | Weight Ratio $H_2O$:Hydrocarbon | Residence Time (MIN) | 2-(4-Hydroxybutyloxy)-Tetrahydrofuran Concentration In Feed | 2-(4-Hydroxybutyloxy)-Tetrahydrofuran Concentration In Product | Percent Removal |
|---|---|---|---|---|---|---|---|
| 1 | 0.2%w $NaH_2PO_4$ | 5.1 | 0.59 | 25 | 431 | 11 | 97 |
| 2 | 0.2%w $NaH_2PO_4$ | 5.0 | 0.65 | 27 | 431 | 12 | 97 |
| 3 | 0.2%w $NaH_2PO_4$ | 5.0 | 0.38 | 27 | 431 | 12 | 97 |
| 4 | 0.2%w $NaH_2PO_4$ | 4.9 | 0.45 | 25 | 431 | 9 | 98 |
| 5 | 0.025%w $NaH_2PO_4$ | 5.2 | 0.55 | 22 | 414 | 26 | 94 |
| 6 | 0.025%w $NaH_2PO_4$ | 5.3 | 0.51 | 24 | 414 | 27 | 94 |
| 7 | 0.025%w $NaH_2PO_4$ | 5.3 | 0.49 | 24 | 414 | 19 | 95 |
| 8 | 0.27%w $NaH_2PO_4$[a] | 6.0 | 0.50 | 24 | 468 | 104 | 78 |
| 9 | 0.27%w $NaH_2PO_4$[a] | 5.9 | 0.51 | 24 | 468 | 88 | 81 |
| 10 | 0.27%w $NaH_2PO_4$[a] | 6.0 | 0.57 | 25 | 468 | 94 | 80 |
| 11 | Distilled water | 7.0 | 0.45 | 27 | 440 | 12 | 97 |
| 12 | Distilled water | 6.7 | 0.50 | 28 | 440 | 38 | 91 |
| 13 | Distilled water | 6.5 | 0.55 | 26 | 440 | 9 | 98 |
| 14 | Distilled water | 7.1 | 0.51 | 43 | 402 | 45 | 89 |
| 15 | Distilled water | 7.5 | 0.59 | 42 | 402 | 31 | 92 |
| 16 | Distilled water | 7.2 | 0.58 | 41 | 402 | 26 | 94 |
| 17 | Soft water[b] | 7.4 | 0.39 | 25 | 427 | 167 | 61 |
| 18 | Soft water[b] | 7.5 | 0.55 | 25 | 427 | 144 | 66 |
| 19 | Soft water[b] | 7.9 | 0.65 | 28 | 427 | 159 | 63 |

[a]Adjusted to pH 6 with 0.1N NaOH
[b]Industrial plant soft water

ILLUSTRATIVE EMBODIMENT II

Oligomer product from a continuous ethylene oligomerization and product recovery process as detailed in Illustrative Embodiment I above was continuously subject to a two stage acid wash at varying pH followed by a single water wash to determine the effect of pH on the removal of 1,4-bis(2-tetrahydrofuryloxy)butane in the $C_{16-18}$ oligomer fraction. The 1,4-bis(2-tetrahydrofuryloxy)butane was selected for study because it appears to be the most difficult to remove of all the butanediol derived degradation products which are found in significant amounts in the oligomer product recovered in accordance with the process described in U.S. Pat. No. 4,020,171. Further, the $C_{16-18}$ fraction was specifically used for determining the effectiveness of the acid wash since the 1,4-bis(2-tetrahydrofuryloxy)butane tends to concentrate in that fraction when the full range oligomer product is fractionated.

The staged hydrolysis and extraction was carried out in two acid contacting stages and one water wash stage, each stage being made up of separate mixing and settling vessels. The mixing vessels employed in all stages were vertically oriented tanks equipped with twin bladed agitators and steam jackets for temperature control. Each mixing vessel was also equipped with a top outlet for the mixed aqueous and oligomer phases and a single bottom inlet for the aqueous extractant phase and the oligomer product phase, said aqueous and oligomer phases being mixed in the line leading to the bottom of the mixing vessel at a point immediately upstream of the inlet. The settling vessels in all cases were horizontally oriented tanks having inlets on one side for the mixed phases and outlets in the top and bottom for the separated oligomer and aqueous phases, respectively. Procedurally, the tests were carried out by using the water phase recovered from the settler of the water washing stage as the aqueous acid base, adding sufficient phosphoric acid to this separated water phase to obtain the desired pH and charging the aqueous acid so obtained to the bottom of the mixer for the second acid contacting stage with the aqueous acid phase recovered from the settler of the second acid contacting stage being passed in combination with fresh oligomer product phase to the bottom of the mixer of the first acid contacting stage.

The conditions for hydrolysis and/or extraction in the two acid contacting stages and the water wash stage were substantially identical except for the pH difference between the wash water and aqueous acid. Specifically, the temperature in each mixing vessel was maintained at 95° C. while the residence time for oligomer product in each stage (combined mixer and settler) was about 60 minutes. Further, the weight ratio of aqueous phase:hydrocarbon phase in each stage was about 0.25:1.0. As indicated in the table below, phosphoric acid was added in varying amounts to the separated aqueous phase from the water washing stage to afford an aqueous acid having a pH between about 3.5 and about 6.0 for use in the aqueous acid contacting stages of the process.

To determine the effectiveness of the hydrolysis and extraction test procedure in removing the 1,4-bis(2-tetrahydrofuryloxy)-butane impurity from the oligomer product, the separated product phase from the water washing stage was passed to a product recovery system comprising a series of distillation columns in which the $C_{16}$ to $C_{18}$ oligomer cut was recovered as a separate fraction. This $C_{16-18}$ fraction was then analyzed by gas-liquid chromatography to determine the amount of 1,4-bis(2-tetrahydrofuryloxy)butane present therein. The results of the tests based on the pH of the aqueous acid employed are given below in Table II.

TABLE II

| pH of Aqueous Acid Extractant | Concentration of 1,4-bis(2-tetra-hydrofuryloxy)butane in the $C_{16-18}$ Oligomer fraction (ppm) |
|---|---|
| 6.0 | 790 |
| 5.0 | 170 |
| 4.6 | 80 |
| 4.1 | 23 |
| 3.9 | 10 |

What is claimed is:

1. In the process for the oligomerization of ethylene to linear alpha-olefins wherein ethylene is oligomerized by contact in liquid phase at elevated pressure with a solution of an oligomerization catalyst composition comprising catalytically active nickel complex in an aliphatic diol solvent to afford a reaction product made up of (1) a liquid solvent phase containing dissolved catalyst, (2) a liquid hydrocarbon phase comprising ethylene oligomers containing dissolved ethylene, catalyst, diol solvent and a minor amount of diol solvent decomposition products and (3) a gaseous ethylene phase, said ethylene oligomers being recovered by separating the liquid hydrocarbon phase from the gaseous ethylene and at least part of the liquid solvent phase under pressure after which the separated liquid hydrocarbon phase is sequentially washed with sufficient aliphatic diol solvent to remove any residual amount of active catalyst, subject to reduced pressure to flash off dissolved ethylene and scrubbed with water to remove residual solvent; the improvement which comprises, contacting the liquid hydrocarbon phase, immediately after water scrubbing, with sufficient aqueous acid at elevated temperature to hydrolyze and extract the diol solvent decomposition products, said aqueous acid having a pH below about 5, and recovering therefrom a liquid hydrocarbon phase substantially free of diol solvent decomposition products.

2. The process according to claim 1 wherein the liquid hydrocarbon phase is contacted with aqueous acid after the said liquid hydrocarbon phase has been scrubbed with water.

3. The process according to claim 2, wherein the aqueous acid has a pH of from about 3.5 to about 4.5.

4. The process according to claim 3 wherein the liquid hydrocarbon phase is contacted with the aqueous acid at a temperature of from about 80° to about 120° C.

5. The process according to claim 4 wherein the aliphatic diol reaction solvent is an alpha-omega alkanediol of 4 to 6 carbon atoms.

6. The process according to claim 5 wherein the aliphatic diol reaction solvent is 1,4-butanediol.

7. The process according to claim 3, wherein the liquid hydrocarbon phase recovered from the aqueous acid contacting step is further washed with water in one or more water scrubbing steps.

8. The process according to claim 1 wherein the aqueous acid contacting and subsequent recovery of the liquid hydrocarbon phase is carried out continuously.

* * * * *